United States Patent [19]

Tsukada et al.

[11] Patent Number: 5,120,885
[45] Date of Patent: Jun. 9, 1992

[54] PROCESS FOR PRODUCING ALCOHOL

[75] Inventors: Kiyoshi Tsukada; Yasuyuki Hattori; Hiroyuki Tamura; Akira Yamamuro; Kunizo Hashiba; Osamu Tabata, all of Wakayama, Japan

[73] Assignee: Kao Corporation, Tokyo, Japan

[21] Appl. No.: 757,053

[22] Filed: Sep. 9, 1991

[30] Foreign Application Priority Data

Sep. 21, 1990 [JP] Japan .................................. 2-253960

[51] Int. Cl.⁵ .................... C07C 29/149; C07C 31/125
[52] U.S. Cl. ...................................... 568/885; 554/194
[58] Field of Search .......................................... 568/885

[56] References Cited

U.S. PATENT DOCUMENTS

| | | | |
|---|---|---|---|
| 2,671,119 | 3/1954 | Mertzweiller | 568/883 |
| 2,815,390 | 12/1957 | Gwynn et al. | 568/883 |
| 4,942,266 | 7/1990 | Fleckenstein et al. | 568/885 |
| 4,954,664 | 9/1990 | Carduck et al. | 568/885 |
| 4,982,020 | 1/1991 | Carduck et al. | 568/885 |

FOREIGN PATENT DOCUMENTS 757484  9/1956  United Kingdom ............... 568/885

Primary Examiner—J. E. Evans
Attorney, Agent, or Firm—Sughrue, Mion, Zinn, Macpeak & Seas

[57] ABSTRACT

A process for producing alcohols comprising catalytically reducing fats and oils or fatty acid esters with hydrogen in the presence of a catalyst for ester reduction is disclosed, wherein the starting oils are first treated at a temperature of from 50° to 200° C. in hydrogen gas or a mixed gas of hydrogen and an inert gas in the presence of a nickel catalyst to yield a sulfur content at not more than 0.6 ppm an acid value (KOH mg/g) of not more than 2. By use of the thus purified starting oils, the catalyst for ester reduction exhibits a prolonged duration.

5 Claims, No Drawings

PROCESS FOR PRODUCING ALCOHOL

FIELD OF THE INVENTION

The invention relates to a process for producing alcohols comprising catalytic reduction of fats and oils or fatty acid esters with hydrogen in the presence of a catalyst for ester reduction. More particularly, it relates to an improved process for producing alcohols in which the duration of the catalyst for ester reduction is extended by using a raw material whose sulfur content has been reduced with a nickel catalyst.

BACKGROUND OF THE INVENTION

Fats and oil and fatty acid esters derived therefrom generally contain at least several to several tens of ppm of sulfur. The terminology, "fats and oils", as used herein means triglycerides and the terminology, "fatty acid esters", as used herein means esters, except triglycerides, of fatty acids and lower or higher alcohols. The raw materials will hereinafter sometimes be referred to as "starting oils" or "starting esters", inclusively. When the sulfur-containing starting oils are catalytically reduced with hydrogen in the presence of a catalyst for ester reduction to produce corresponding alcohols, a trace amount of sulfur compounds present therein acts as a catalyst poison to cause a marked reduction of duration of catalyst life.

The inventors made a study of purification methods for the starting oils to reduce the sulfur content thereof and, as a result, brought out the following points.

1) Problems of Purification by Distillation

When methyl esters of fatty acids which are derived from natural fats and oils in a conventional manner are subjected to distillation to a yield of 90% or 98%, the sulfur content can be reduced to 10% or 20%, respectively, of the initial content. However, where fatty acid methyl esters which are usually available or prepared are distilled for meeting the purpose of sulfur content reduction, there is an unavoidable loss of at least 5%, and the alkyl distribution of the starting material varies largely.

In the case of fats and oils or esters of fatty acids and higher alcohols, because of the high boiling point thereof, it is difficult to remove the sulfur compounds from such starting materials by distillation.

2) Problems of Purification with Catalyst for Desulfurization

In the field of petroleum refining, molybdenum or tungsten catalysts are used for removing sulfur compounds from light oil and heavy oil (refer to *Shokubai Process Kaqaku*, Tokyo Kagaku Dojin Shuppan).

The catalysts require temperatures of 300° C. or higher for manifestation of the desulfurization activity. If fats and oils or fatty acid esters are hydrogenated in such high temperatures, hydrogenolysis of the ester group is attended by an increase in acid value and a marked increase of decomposition products of the starting material. In addition, a catalyst component is dissolved by the produced fatty acids which adversely affects selectivity of the catalyst in the ester reduction reaction.

SUMMARY OF THE INVENTION

Accordingly, an object of the present invention is to provide an economical and efficient purification technique as a substitute for distillation for reducing the sulfur content of starting oils used for the production of alcohols.

Another object of the present invention is to provide a process for producing alcohols from fats and oils or fatty acid esters having a reduced sulfur content.

The inventors have conducted extensive investigations to establish such a purification technique and, as a result, found that starting oils having a reduced sulfur content can be obtained in good yield by treatment with a nickel catalyst in hydrogen gas or a mixed gas of hydrogen and an inert gas, preferably in the presence of a monohydric or polyhydric alcohol having from 1 to 18 carbon atoms.

Accordingly, the present invention provides a process for producing alcohols comprising catalytically reducing fats and oils or fatty acid esters with hydrogen in the presence of a catalyst for ester reduction, wherein said fats and oils or fatty acid esters are first treated at a temperature of from 50° to 200° C. in hydrogen gas or a mixed gas of hydrogen and an inert gas in the presence of a nickel catalyst to yield a sulfur content of not more than 0.6 ppm, preferably not more than 0.3 ppm, and an acid value (KOH mg/g; hereinafter referred to as AV) of not more than 2.

DETAILED DESCRIPTION OF THE INVENTION

In the production of aliphatic alcohols by catalytically reducing fats and oils or fatty acid esters thereof with hydrogen in the presence of a catalyst for ester reduction, the catalyst life or durability is influenced greatly by the quality of the starting oils. The inventors have examined closely impurities in the starting oils which have great influences on the duration of the catalyst for ester reduction and found that free fatty acids act as an extremely strong catalyst poison, in addition to sulfur compounds and halogen compounds conventionally known as catalyst poisons. Sulfur compounds and halogen compounds are known generally as poisons of catalysts for hydrogenation, and it is desirable to reduce those poisonous substances as much as possible when conducting hydrogenation reactions. Since the halogen content of usual starting oils is very low, reduction of the sulfur content is the most important subject to consider. Further, industrially employed catalysts for ester reduction are copper-chromium catalysts and copper-zinc catalysts which are susceptible to corrosion by free fatty acids. Therefore, it is also important to minimize the concentration of free fatty acids in the starting oils.

To determine permissible concentrations of sulfur compounds and free fatty acids in the starting oils for production of alcohols, the inventors carried out experiments by using methyl esters derived from coconut oil or palm kernel oil in a usual manner with a copper-chromium catalyst or a copper-zinc catalyst (see Reaction Examples 1 and 2 hereinafter described). For comparison, methyl esters obtained by distillation of the same starting oil (distillation yield: 90%) which have a sulfur content of from 0.3 to 0.4 ppm and an AV of 0.1 or less were used. It was confirmed that substantially the same catalyst durability as obtained when using distilled methyl esters can be assured by using a starting material having a sulfur content of not more than 0.6 ppm and an AV of not more than 2.

In the present invention, the sulfur content in the starting oils is determined by means of a Dohrmann type low concentration sulfur analyzer (System 701, manufactured by Rosemount Analytical, Inc.).

Sulfur compounds present in starting oils cannot be removed completely by common purification procedures such as treatment with an adsorbent, alkali treatment and steaming. Those purification procedures, even when sufficiently performed, still leave about 3 to 5 ppm of a sulfur content. Attempts to reduce further the sulfur content by such customary purification operations were unsuccessful. Thus, under the present situation, there has been no means but to conduct purification by distillation. On the other hand, free fatty acids can be reduced easily by common purification procedures, such as alkali treatment and steaming.

Fats and oils to be used in the present invention as the starting oil include vegetable and animal fats and oils such as coconut oil, palm oil, palm kernel oil, soy bean oil, rape seed oil, beef tallow, pork tallow, fish oils and hydrogenated fats and oils of these fats and oils.

Fatty acid esters which can be used in the present invention include those derived from the above-mentioned fats and oils and esters of aliphatic carboxylic acids having 1 to 24 carbon atoms with lower or higher alcohols having 1 to 24 carbon atoms, such as saturated or unsaturated and straight chain or branched alcohols having 1 to 24 carbon atoms.

Useful examples of the aliphatic carboxylic acid include lauric acid, myristic acid, palmitic acid, stearic acid, eicosanic acid, docosanic acid, oleic acid and erucic acid.

Useful examples of the lower and higher alcohols include methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6hexanediol, 1,10-decanediol, cycrohexanol, benzyl alcohol, diethylene glycol, glycerol and trimethylol propane.

In the process of the present invention, the customary distillation purification step of the starting oils or esters may be conducted prior to the treatment of the starting oils or esters in hydrogen gas or a mixed gas of hydrogen and an inert gas in the presence of a nickel catalyst.

The nickel catalyst which can be used in the present invention usually is supported on or mixed with a carrier. The nickel content ranges from 10 to 200% by weight based on the carrier. The carrier to be used is selected from known carriers, e.g., silica, alumina, silica-alumina, zeolite, diatomaceous earth, acid clay, titania, zirconia and activated carbon. The form of the nickel-on-carrier catalyst is selected appropriately according to the treating system from a powder form and molded forms such as a spherical or column form. The catalyst is activated by reduction with hydrogen on use. In some cases, a catalyst previously activated by reduction and stabilized in a known manner may be used as such or after re-activation by reduction.

The treatment of the starting oils may be effected continuously, semi-batchwise or batchwise. For mass treatment, a continuous system is recommended. Continuous treatment can be carried out in any of many widely practiced reaction systems, such as a fixed bed system, a mobile bed system, a fluidized bed system or systems used in, for example, petroleum refining, e.g., catalytic desulfurization, catalytic cracking and catalytic reforming. In general, where the starting oils have a relatively low sulfur content, a fixed bed system in which a catalyst can be used in a high concentration is preferred. Where the starting oils have a high sulfur content, the treatment may be performed in a mobile bed or fluidized bed system in which a spent catalyst having reduced activity can be exchanged continuously.

According to the present invention, the starting oils are treated in the presence of the above-described nickel catalyst in, for example, a fixed bed continuous reaction system under the following conditions.

Hydrogen or an inert gas mixture containing at least 1% by volume of hydrogen is used as flowing treatment gas. Inert gases to be used include, for example, nitrogen, argon, helium and methane. The flow rate of hydrogen or a hydrogen-containing mixed gas is determined arbitrarily within such a range that the molar ratio of hydrogen to the ester group content of the starting oils which is calculated from the saponification value (KOH mg/g; hereinafter abbreviated as SV) is from 0.1 to 300. The flowing gas pressure is from 0.1 to 500 $kg/cm^2$, and preferably from 1 to 300 $kg/cm^2$. As the hydrogen to ester group molar ratio become smaller, the increase in AV is remarkable.

The treating temperature is selected from 50° to 250° C., preferably from 80° to 200° C. At lower temperatures, the efficiency of sulfur compound removal and the nickel catalyst durability are reduced. At higher temperatures, an increase in AV is observed and the amount of by-products due to cracking of the starting oils increases. A preferred treating temperature is therefore 200° C. or less.

Flow velocity of the starting oil is controlled as to give a volume ratio to the reaction tower per hour (liquid hourly space velocity, hereinafter abbreviated as LHSV) of from 0.1 to 5.0. As the flow velocity decreases, although the sulfur compound removal efficiency increases, the AV of the resulting oil markedly increases. Such a low flow velocity is also disadvantageous from the view point of productivity.

When the starting oils are purified under the above-mentioned conditions, it is natural that some conditions selected for reducing the sulfur content to 0.6 ppm or less should result in an increase in AV. Where the purification treatment is conducted under such conditions which require inhibition in the increase of AV, it is permitted to add previously a mono- or polyhydric alcohol having from 1 to 18 carbon atoms to the starting oil whereby free fatty acids produced during the purification treatment are esterified with the added alcohol to reduce the AV to an acceptable level. The alcohol is added in an amount of from 10 to 1000 moles, and preferably from 20 to 500 moles, per mol of free fatty acids produced or estimated to be produced under such conditions. Examples of usable mono- or polyhydric alcohols having from 1 to 18 carbon atoms are methanol, ethanol, propanol, isopropanol, butanol, sec-butanol, t-butanol, pentanol, hexanol, heptanol, octanol, decanol, dodecanol, tetradecanol, hexadecanol, octadecanol, ethylene glycol, propylene glycol, butanediol and glycerol. Among them, methanol is preferred.

The thus purified starting oil having a sulfur content of 0.6 ppm or less and an AV of 2 or less is then subjected to catalytic reduction with hydrogen using a copper-based catalyst for ester reduction to be converted to the corresponding alcohols. The copper-based catalyst for ester reduction is a catalyst mainly comprising copper, typically exemplified by known catalyst systems, e.g., copper-chromium, copper-zinc, copper-iron-aluminum and copper-silica. The ester reduction may be effected in the presence of the catalyst either in a liquid phase suspended bed system or in a fixed bed system.

When a liquid phase suspended bed system is employed, the catalyst is preferably used in an amount of from 0.1 to 20% by weight based on the starting and oils and/or esters, though the catalyst amount may optionally be selected depending on the reaction temperature or the reaction pressure within a range in which a reaction rate sufficient for practical production can be obtained. The reaction temperature may range from 160° to 350° C., preferably from 200° to 280° C., while the reaction pressure may range from 1 to 350 kg/cm², preferably from 30 to 300 kg/cm².

When a fixed bed system is employed, the catalyst is employed in a molded form such as column, pellet or spherical form. The reaction temperature may range from 130° to 300° C., preferably from 160° to 270° C., while the reaction pressure may range from 0.1 to 300 kg/cm². LHSV preferably ranges from 0.5 to 5 in terms of production or reaction efficiency, though it may be optionally selected depending on the reaction conditions.

In the case of liquid phase suspended bed system, the purified starting oil can be obtained by filtrating off the catalyst therefrom, while in the case of a fixed bed system, filtration step of the catalyst is not required.

The present invention is now illustrated in greater detail with reference to Referential Examples and Reaction Examples, but it should be understood that the present invention is not deemed to be limited thereto. All the percents, parts, and ratios are by weight unless otherwise indicated.

REFERENTIAL EXAMPLE 1

A high pressure reaction tube having an inner diameter of 28 mm was packed with 270 cc of a commercially available extrusion-molded nickel/silica-alumina catalyst (product of Nissan Girdler Co., Ltd.; nickel content: 50%; diameter: 1.5 mm; length: 3 to 6 mm). Nitrogen gas containing 5 to 60% by volume of hydrogen was passed through the catalyst bed at a flow rate of about 140 l/hr under normal pressure at 150° to 155° C. for 7.5 hours to pretreat the catalyst. Then, a coconut oil fatty acid methyl ester and a hydrogen-containing gas were made to flow downward in parallel under various conditions to remove the sulfur content of the starting ester. The coconut oil fatty acid methyl ester used had the following analytical values.

| | |
|---|---|
| SV (KOH mg/g): | 255.7 |
| AV (KOH mg/g): | 0.04 |
| Hydroxyl value (KOH mg/g): (hereinafter abbreviated as OHV) | 5.8 |
| IV (iodine value): | 8.4 |
| Water content: | 0.05% |
| Sulfur content: (hereinafter abbreviated as S) | 3.3 ppm |

Influence of Reaction Temperature

The influence of reaction temperature on S and AV was examined by conducting the purification treatment at a varied temperature with the hydrogen pressure, LHSV of the starting ester and the hydrogen to ester molar ratio being fixed at 100 kg/cm², 1.5, and 1, respectively. The results obtained are shown in Table 1 below.

TABLE 1

| Temperature (°C.) | 60 | 100 | 150 | 170 |
|---|---|---|---|---|
| S (ppm) | 0.60 | 0.52 | 0.41 | 0.36 |

TABLE 1-continued

| AV | 0.4 | 0.7 | 1.4 | 2.5 |
|---|---|---|---|---|

Influence of Reaction Pressure

The influence of reaction pressure on S and AV was examined by conducting the purification treatment under a varied reaction pressure with LHSV of the starting ester, hydrogen to ester molar ratio and reaction temperature being fixed at 1.5, 1, and 150° C., respectively. The results obtained are shown in Table 2 below.

TABLE 2

| Pressure (kg/cm²) | 10 | 40 | 100 | 140 |
|---|---|---|---|---|
| S (ppm) | 0.79 | 0.56 | 0.41 | 0.20 |
| AV | 0.4 | 0.7 | 1.4 | 2.0 |

Influence of Hydrogen/Ester Molar Ratio

The influence of hydrogen to ester molar ratio on S and AV was examined by conducting the purification treatment at a varied hydrogen to ester molar ratio with the hydrogen pressure, LHSV of the starting ester, and reaction temperature being fixed at 100 kg/cm², 1.5, and 150° C., respectively. The results obtained are shown in Table 3 below.

TABLE 3

| H₂/ester molar ratio | 1 | 13 | 50 |
|---|---|---|---|
| S (ppm) | 0.41 | 0.48 | 0.43 |
| AV | 1.4 | 0.8 | 0.6 |

REFERENTIAL EXAMPLE 2

The same purification procedure of Example 1 was repeated, except for replacing the coconut oil fatty acid methyl ester with a deacidified coconut oil. The starting oil used here had the following analytical values.

| | | | |
|---|---|---|---|
| SV: 243.9 | | AV: 0.02 | |
| OHV: 4.9 | | IV: 17.7 | |
| Water content: 0.05% | | S: 4.0 ppm | |

The influence of reaction temperature on S and AV was examined by conducting the purification treatment at a varied temperature with the hydrogen pressure, LHSV of the starting oil and hydrogen/ester molar ratio being fixed at 150 kg/cm², 1.5, and 50, respectively. The results obtained are shown in Table 4 below.

TABLE 4

| Temperature (°C.) | 100 | 150 | 170 |
|---|---|---|---|
| S (ppm) | 0.59 | 0.37 | 0.28 |
| AV | 0.3 | 1.0 | 1.6 |

REFERENTIAL EXAMPLE 3

The same starting ester as used in Example 1 was purified by using the same reactor a used in Example 1 under the following conditions.

A hydrogen/nitrogen mixed gas having a varied hydrogen concentration was used. The starting ester was fed at an LHSV of 1.5 and the gas flow rate was altered so as to have a hydrogen/ester molar ratio of 13. The reaction pressure and temperature were fixed at 200 kg/cmhu 2 and 150° C., respectively. The results obtained are shown in Table 5 below.

TABLE 5

| $H_2$ Concentration (vol. %) | 1 | 20 | 50 |
|---|---|---|---|
| S (ppm) | 0.60 | 0.52 | 0.30 |
| AV | 0.4 | 0.5 | 0.6 |

REFERENTIAL EXAMPLE 4

To examine the effect of alcohol addition to the starting ester on inhibiting on increase of AV, the same procedure of Example 1 was repeated, except for adding methanol to the starting ester at a varied molar ratio to the starting ester and conducting the treatment at a hydrogen pressure of 100 kg/cm$^2$, at the LHSV of the starting ester of 1.5, at a hydrogen/ester molar ratio of 1 and at a temperature of 150° C. or 170° C. The results obtained are shown in Table 6 below.

TABLE 6

| Temperature (°C.) | 150 | 150 | 170 | 170 | 170 | 170 |
|---|---|---|---|---|---|---|
| Methanol/ester molar ratio | 0 | 0.6 | 0 | 0.3 | 0.6 | 3.0 |
| S (ppm) | 0.40 | 0.38 | 0.36 | 0.35 | 0.33 | 0.35 |
| AV | 1.4 | 0.6 | 2.0 | 1.7 | 1.3 | 0.9 |

REFERENTIAL EXAMPLE 5

A high pressure reaction tube having an inner diameter of 10 mm was packed with 15 cc of the same nickel/-silica-alumina catalyst used in Example 1 and the catalyst bed was heated to a temperature of from 100° to 190° C. in a nitrogen gas stream containing 5% by volume of hydrogen. When the temperature reached 190° C., the hydrogen concentration was stepwise increased finally to 100% by volume at 200° C., where the pretreatment of the catalyst was continued for 4 hours.

Then, a palm kernel oil fatty acid methyl ester and hydrogen were made to flow upward in parallel under various conditions to remove the sulfur compound of the starting ester. The palm kernel oil fatty acid methyl ester had the following analytical values.

| SV: 242.9 | AV: 0.07 |
|---|---|
| OHV: 8.1 | IV: 18.5 |
| Water content: 0.02% | S: 2.20 ppm |

Influence of Reaction Temperature

The influence of reaction temperature on S and AV was examined by conducting the purification treatment at a varied temperature with the hydrogen pressure, LHSV of the starting ester and the hydrogen/ester molar ratio being fixed at 230 kg/cm$^2$, 2.0, and 50, respectively. The results obtained are shown in Table 7 below.

TABLE 7

| Temperature (°C.) | 100 | 120 | 140 |
|---|---|---|---|
| S (ppm) | 0.28 | 0.17 | 0.08 |
| AV | 0.07 | 0.15 | 0.27 |

Influence of Flow Velocity of Starting Oil

The influence of the flow velocity (LHSV) of the starting ester on S and AV was examined by conducting the purification treatment at a varied LHSV with the hydrogen pressure, hydrogen/ester molar ratio and reaction temperature being fixed at 230 kg/cm$^2$, 50, and 120° C., respectively. The results obtained are shown in Table 8 below.

TABLE 8

| LHSV (/hr) | 1.0 | 2.0 | 3.0 |
|---|---|---|---|
| S (ppm) | 0.14 | 0.17 | 0.27 |
| AV | 0.18 | 0.15 | 0.12 |

Influence of Hydrogen/Ester Molar Ratio

The influence of the hydrogen/ester molar ratio on S and AV was examined by conducting the purification treatment at a varied hydrogen/ester molar ratio with the hydrogen pressure, LHSV of the starting ester and reaction temperature being fixed at 230 kg/cm$^2$, 3.0, and 150° C., respectively. The results obtained are shown in Table 9 below.

TABLE 9

| $H_2$/ester molar ratio | 15 | 50 |
|---|---|---|
| S (ppm) | 0.14 | 0.13 |
| AV | 0.37 | 0.34 |

The yield of purification in any of Examples 1 to 5 was substantially 100% with no loss of purification.

REFERENTIAL EXAMPLE 6

A palm kernel oil fatty acid methyl ester having the following analytical values was purified by commonly employed distillation to reduce the sulfur content.

| SV: 242.6 | AV: 0.02 |
|---|---|
| OHV: 4.9 | IV: 17.8 |
| Water content: 0.03% | S: 3.6 ppm |

Six kilograms of the above methyl ester were charged in a 10 l-volume distillation column and distillation was carried on under the reduced pressure of from 1 to 2 mmHg. After about 3 kg of the starting ester had distilled off, the residue was replenished with a fresh starting ester and the distillation was continued further to purify 8.02 kg of the methyl ester in total. The sulfur content in the distillate was measured to determine the sulfur content vs. the rate of distillation. The results obtained are shown in Table 10 below.

TABLE 10

| Rate of distillation | 70.2 | 79.8 | 90.1 | 95.3 | 98.0 |
|---|---|---|---|---|---|
| Degree of vacuum (mmHg) | 2.0 | 1.1 | 1.1 | 1.0 | 1.0 |
| Temperature of distillation bottom (°C.) | 187 | 187 | 196 | 210 | 210 |
| S (ppm) | 0.17 | 0.25 | 0.33 | 0.49 | 0.72 |

When the rate of distillation was 95%, the residual ester at the bottom was found to comprise 80% or more of methyl esters of fatty acids having 18 carbon atoms. This indicates that the conventional purification by distillation unavoidably is attended by an increased loss of long-chain ($C_{16}$ to $C_{18}$) methyl esters.

REACTION EXAMPLE 1

Each of the purified methyl esters obtained in the foregoing Referential Examples 1, 3, and 6 and an untreated methyl ester as shown in Table 11 below was reduced in the presence of a catalyst for ester reduction to evaluate duration of the catalyst for ester reduction.

TABLE 11

| Starting Ester | Referential Example No. | Purification Conditions | S (ppm) | AV |
|---|---|---|---|---|
| A | Referential Example 3 | 150° C., 200 kg/cm², LHSV = 1.5, H₂/ester molar ratio = 13 (H₂: 50% by volume) | 0.30 | 0.6 |
| B | Referential Example 1 | 150° C., 40 kg/cm², LHSV = 1.5, H₂/ester molar ratio = 1 | 0.56 | 0.7 |
| C | Referential Example 1 | 150° C., 10 kg/cm², LHSV = 1.5, H₂/ester molar ratio = 1 | 0.79 | 0.4 |
| D | Referential Example 6 | rate of distillation = 90.1% | 0.33 | 0.05 |
| E | — | untreated | 3.3 | 0.05 |

The catalyst used here was the copper-zinc on titania catalyst disclosed in JP-A-1-305042 (corresponding to U.S. Pat. No. 4,918,248) having a composition of $CuO:ZnO:TiO_2 = 47.5:2.5:50.0$ (%) (the term "JP-A" as used herein means an "unexamined published Japanese patent application").

In a 0.5 l-volume autoclave equipped with a rotary stirrer were charged 150 g of each of the starting methyl esters A to E and 3.75 g of the catalyst. The catalyst was activated in a hydrogen flow at a pressure of 10 kg/cm² and at a temperature of 200° C. for 2 hours. After the inner temperature was raised up to 230° C., the hydrogen pressure was elevated to 120 kg/cm², and reduction of the methyl ester was commenced at a stirring speed of 800 rpm and at a hydrogen flow rate of 5 l/min. The reaction system was sampled appropriately in the course of the reaction and analyzed to obtain the conversion of the starting ester by gas chromatography. The reaction was adjusted as a first-order reaction with respect to the ester concentration and the rate constant per gram of the catalyst before activation was taken as a criterion of catalyst activity.

After completion of the reaction, the catalyst was separated from the alcohol produced by filtration and reused in the next reaction. The reaction was repeated 10 times under the same conditions and the rate constant was obtained per reaction. A reduction of activity per reaction was calculated according to the following equation. In every experiment, the plots of rate constant vs. number of times of catalyst recovery revealed good linearity.

$$\text{Activity Reduction (\%/reaction)} = \frac{k_1 - k_{10}}{k_1} \times 100(\%)/\text{number of times of use}$$

wherein $k_1$ represents rate constant at the first time; and $k_{10}$ represents rate constant at the tenth time of catalyst recovery.

The results obtained are shown in Table 12 below.

TABLE 12

| Starting Ester | S (ppm) | AV | Activity Reduction (%/reaction) |
|---|---|---|---|
| A | 0.30 | 0.6 | 0.74 |
| B | 0.56 | 0.7 | 0.65 |
| C | 0.79 | 0.4 | 3.18 |
| D | 0.33 | 0.05 | 0.75 |
| E | 3.3 | 0.05 | 6.75 |

It can be seen from the results in Table 12 that starting esters A and B purified by treatment with a nickel/-silica-alumina catalyst and having a sulfur content of not more than 0.6 ppm show an equal activity reduction to the distilled methyl ester (starting ester D). Accordingly, it was confirmed that activity duration of the catalyst can be prolonged by the process according to the present invention.

REACTION EXAMPLE 2

Each of the purified methyl esters obtained in the foregoing Referential Examples 1, 2, 5 and 6 as shown in Table 13 below was reduced in the presence of a catalyst for ester reduction to evaluate catalyst duration.

TABLE 13

| Starting Ester | Referential Example No. | Purification Conditions | S (ppm) | AV |
|---|---|---|---|---|
| F | Referential Example 5 | 100° C., 230 kg/cm², LHSV = 2.0, H₂/ester molar ratio = 50 | 0.28 | 0.07 |
| G | Referential Example 2 | 150° C., 150 kg/cm², LHSV = 1.5, H₂/ester molar ratio = 50 | 0.37 | 1.0 |
| H | Referential Example 2 | 170° C., 150 kg/cm², LHSV = 1.5, H₂/ester molar ratio = 50 | 0.28 | 1.6 |
| I | Referential Example 1 | 170° C., 100 kg/cm², LHSV = 1.5, H₂/ester molar ratio = 1 | 0.36 | 2.5 |
| D | Referential Example 6 | distillation rate = 90.1% | 0.33 | 0.05 |

The catalyst was a commercially available copper-chromium catalyst. The ester reduction activity and activity duration were evaluated in the same manner as in Reaction Example 1, except for using 7.50 g (5.0% based on the starting ester) of the catalyst and changing the reaction temperature to 250° C. The results obtained are shown in Table 14 below.

TABLE 14

| Starting Ester | S (ppm) | AV | Activity Reduction (%/reaction) |
|---|---|---|---|
| F | 0.28 | 0.07 | 0.60 |
| G | 0.37 | 1.0 | 0.80 |
| H | 0.28 | 1.6 | 0.76 |
| I | 0.36 | 2.5 | 1.73 |
| D | 0.33 | 0.05 | 0.67 |

The results in Table 14 prove that an AV exceeding 2 results in a marked reduction of catalyst activity. It is seen that the activity reduction of the starting esters having an AV of 2 or less (F, G, and H) is substantially equal to that of the distilled material (D).

As described and demonstrated above, the present invention provides a highly economical and highly efficient process for purifying starting oils for production of alcohols, by which the sulfur content of the starting oils can be reduced to such a level that does not cause a great reduction of activity of a catalyst for ester reduction to be used in the production of alcohols while maintaining a purification yield of 100%. The sulfur compound removal efficiency reached by the instant purification process is several times higher than that of the customary distillation purification. Thus, the present invention makes it possible to produce alcohols while assuring an extended duration of a catalyst for ester reduction by using the thus purified starting oils.

While the invention has been described in detail and with reference to specific examples thereof, it will be apparent to one skilled in the art that various changes and modifications can be made therein without departing from the spirit and scope thereof.

What is claimed is:

1. A process for producing alcohols comprising reducing fats and oils or fatty acid esters with hydrogen in the presence of a catalyst for ester reduction, wherein said fats and oils or fatty acid esters are first treated at a temperature of from 50° to 200° C. in hydrogen gas or a mixed gas of hydrogen and an inert gas in the presence of a nickel catalyst to yield a sulfur content of not more than 0.6 ppm and an acid value of not more than 2.

2. The process of claim 1, wherein said treatment of the fats and oils or fatty acid esters is carried out in a continuous system.

3. The process of claim 2, wherein said continuous system is a fixed bed continuous system.

4. The process of claim 1, wherein said treatment of the fats and oils or fatty acid esters is carried out in the presence of a mono- or polyhydric alcohol having from 1 to 18 carbon atoms.

5. The process of claim 1, wherein said sulfur content of the fats and oils or fatty acid esters is not more than 0.3 ppm.

* * * * *